United States Patent [19]
Woziwodzki

[11] 4,122,094
[45] Oct. 24, 1978

[54] SEPARATION OF THE ISOMERS OF TOCOPHEROL BY LIQUID/SOLID CHROMATOGRAPHY

[75] Inventor: Hiltrud E. Woziwodzki, North Bergen, N.J.

[73] Assignee: Lever Brothers Company, New York, N.Y.

[21] Appl. No.: 796,642

[22] Filed: May 13, 1977

Related U.S. Application Data

[63] Continuation of Ser. No. 694,104, Jun. 9, 1976, abandoned.

[51] Int. Cl.² .......................................... C07D 311/72
[52] U.S. Cl. ............................... 260/345.6; 210/31 C
[58] Field of Search ................ 210/31 C, 24 C, 24 P; 260/345.5, 345.6, 31 C

[56] References Cited

U.S. PATENT DOCUMENTS

| | | | |
|---|---|---|---|
| 2,350,713 | 6/1944 | Baxter et al. | 260/345.5 |
| 3,122,565 | 2/1964 | Kijima et al. | 260/345.6 |
| 3,153,055 | 10/1964 | Brown et al. | 260/345.6 |

OTHER PUBLICATIONS

Cavins et al., Cereal Chem., 51, 605, (1974).
Whittle et al., Analyst, 92, 423, (1967).

*Primary Examiner*—Nicky Chan
*Attorney, Agent, or Firm*—Michael J. Kelly; Melvin H. Kurtz; James J. Farrell

[57] ABSTRACT

Methods of separating the alpha-, beta-, gamma-, and delta-tocopherol isomers from mixtures containing these isomers by liquid/solid chromatography techniques using a liquid phase comprising chloroform substantially free of ethanol are disclosed. These methods are particularly suitable for the quantitative determination of these isomers in vegetable oils and in margarines, and for the isolation of substantially pure isomeric forms from naturally occurring mixtures and from the by-products of crude edible oil refinement.

18 Claims, 4 Drawing Figures

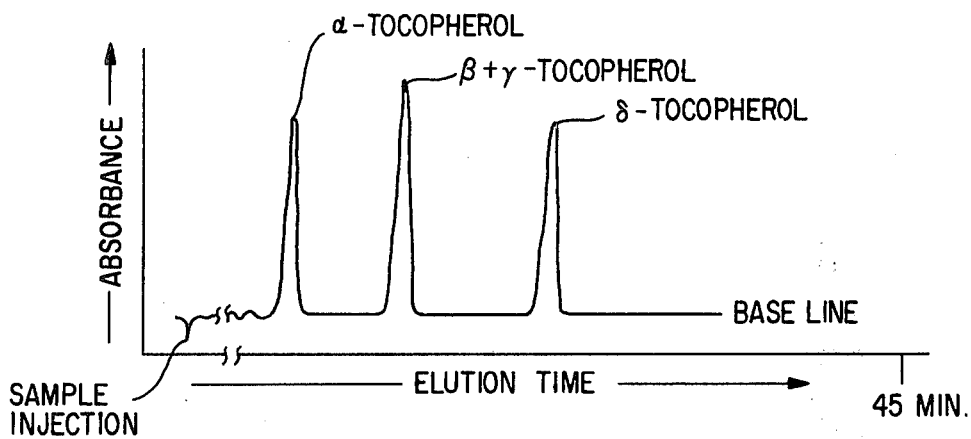
FIG. 1 HPLC CHROMATOGRAM OF TOCOPHEROL ISOMERS USING REAGENT GRADE $CHCL_3$
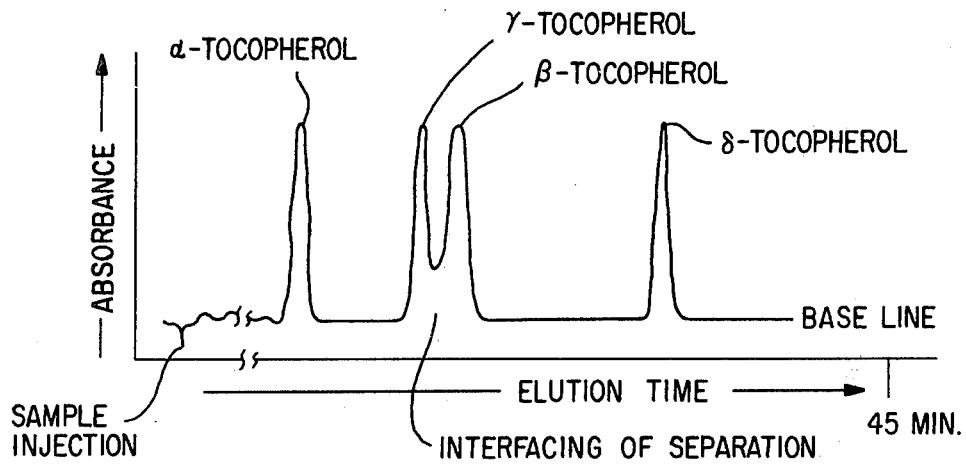
FIG. 2 HPLC CHROMATOGRAM OF TOCOPHEROL ISOMERS USING TREATED $CHCL_3$
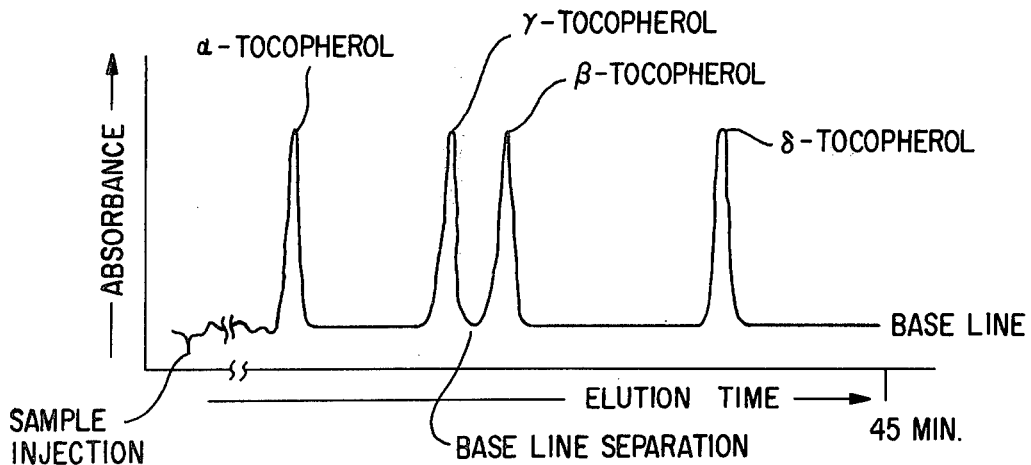
FIG. 3 HPLC CHROMATOGRAM OF TOCOPHEROL ISOMERS USING "ETHANOL-FREE" $CHCL_3$

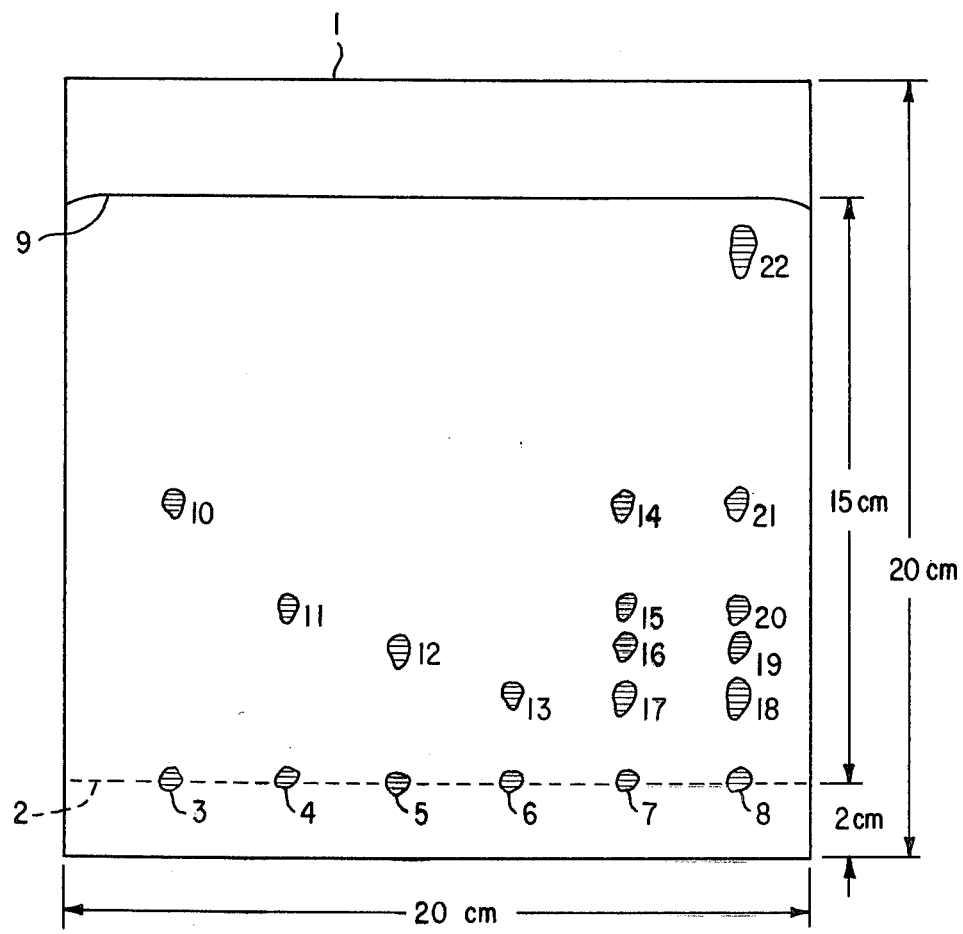
FIG. 4 THIN-LAYER CHROMATOGRAPHY (TLC) OF α-, β-, γ-, AND δ- TOCOPHEROL STANDARDS AND MIXTURES (INCLUDING MIXTURE CONTAINED IN MARGARINE).

SEPARATION OF THE ISOMERS OF TOCOPHEROL BY LIQUID/SOLID CHROMATOGRAPHY

This is a continuation of application Ser. No. 694,104, filed June 9, 1976, now abandoned.

BACKGROUND OF THE INVENTION

This invention relates to methods of separating the alpha, beta, gamma and delta ($\alpha$, $\beta$, $\gamma$ and $\delta$ respectively) isomers of tocopherol from mixtures containing these isomers. This invention is especially significant in that it is now possible to achieve a complete separation of the gamma and beta forms which heretofore had not been truly separated. Moreover, this invention provides a quick and simple means for making such a separation without the need for complicated derivatization reactions or other destructive techniques. This invention is very significant with respect to vitamin E chemistry in that all the naturally occurring forms of this vitamin (i.e. the tocopherol isomers) can be separated and isolated.

Within the last decade, the group of naturally occurring compounds possessing vitamin E activity has been shown to include alpha-tocopherol (5,7,8-trimethyltocol), beta-tocopherol (5,8-dimethyltocol), gamma-tocopherol (7,8-dimethyltocol) and delta-tocopherol (8-methyltocol). The structures of these compounds are given below for comparative and illustrative purposes as formulas I, II, III and IV respectively.

E deficiency symptoms in the body. These effects, more specifically, the symptoms of vitamin E deprivation were discovered to vary according to the particular species of animal involved. As a result of the lack of knowledge as to the actual composition, vitamin E "activity" was used for many years to designate the amount of dosage required for a particular agent to cure a particular deficiency symptom.

Finally, four naturally occurring compounds having vitamin E activity were isolated and identified. These substances were designated as $\alpha$, $\beta$-, $\gamma$-, and $\delta$-tocopherol. Chemically, all four are methyl derivatives of tocol[2-methyl-2-(4',8',12'-trimethyltridecyl)-6-chromanol]. Simply, the structures are methyl derivatives of a chromane ring type structure of the general formula

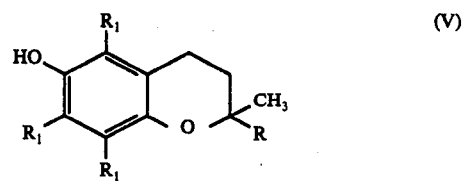

(V)

wherein R is 4,8,12-trimethyl-n-tridecane, and $R_1$ is methyl or hydrogen where at least one $R_1$ is methyl. Additional compounds analogous to the tocopherols have also been characterized. These compounds are the

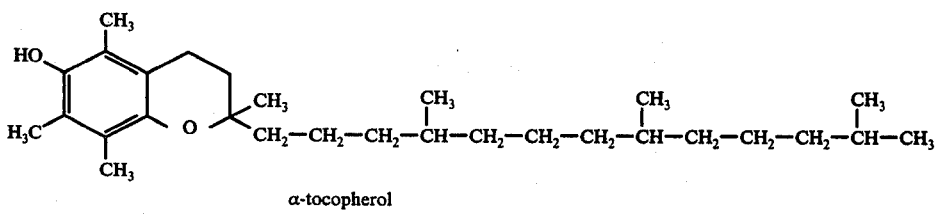

$\alpha$-tocopherol (I)

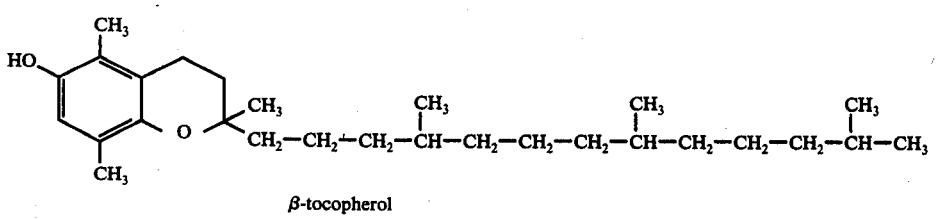

$\beta$-tocopherol (II)

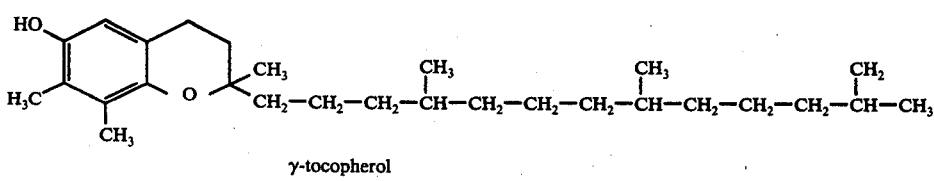

$\gamma$-tocopherol (III)

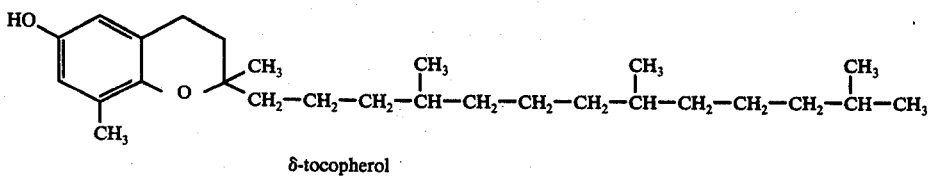

$\delta$-tocopherol (IV)

The term "vitamin E" originally denoted a partially characterized material in vegetable oils that was found to be essential for the rat to maintain fertility. First discovered in 1922, it was found that more than one naturally occurring substance and several synthetic compounds acted like, or had some effect upon vitamin E methyl derivatives of tocotrieno[2-methyl-2-(4',8',12'-trimethyltrideca-3',7',11'-trienyl)-6-chromanol]. The main difference structurally in the latter compounds is that they contain three unsaturated bonds in the side chain but are otherwise of the same general formula as (V) except that R would be the formula

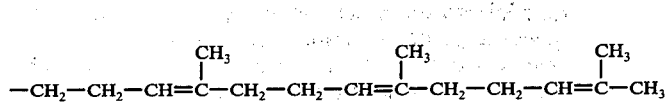

$$\text{(VI)}$$

Although the tocopherols and tocotrienols appear to be of rather similar chemical structure, they have been found to exhibit markedly different biological properties. In fact, distinct differences in bioactivity have been noted for the different isomers of tocopherol alone. Alpha-tocopherol, with its completely methylated ring and saturated side chain, possesses the highest biological activity. Because of this high potency, the term "α-tocopherol" is now gaining wide use as an identification of "vitamin E."

Alpha-tocopherol and its acetate are the forms most used commercially. The naturally occurring d form is the most active isomer physiologically with the racemic synthetic dl-α-tocopherol and its esters being less potent on a weight for weight basis than the d form. Alpha-tocopherol acetate is the principal commercial form of vitamin E in medicine. Additional uses for the tocopherols include, in food technology, their use as antioxidants to retard rancidity in fatty materials. These compounds have also, with some degree of notariety, been employed as actives for aerosol deodorants. Additional uses include other cosmetics including "coldcreams." Because of their antioxidant activity, these compounds are theorized to have possible anticancer activity especially in those forms suspected of being caused by free radical initiation. This particular activity is somewhat speculative due to lack of knowledge or at least hard data in this field.

The tocopherols are found distributed in many foods in an unesterified form. The highest concentrations are found in the cereal grain oils. Crude corn and wheat oils for example may contain 200 mg of tocopherol per 100 g of oil. There seems to be, however, great variation with respect to what particular oil is used. Certain vegetable oils, such as coconut oil, are practically devoid of tocopherols. Similarly, the proportion of the various isomers also varies widely. For example, about 90% of the tocopherol in safflower oil is α-tocopherol whereas only about 20% of corn and soybean oil is in the alpha form. The gamma form predominates in corn oil, whereas both the gamma and delta forms predominate in soybean oil. Wheat oils on the other hand have mixtures of tocopherol with up to 65% in the beta form.

Significant losses of vitamin E may occur during the processing and cooking of foods. The degree of loss is dependent of course upon the mode of process, etc. The amount of tocopherol left in refined salad oil, for example, depends upon the severity of the refining process.

A detailed discussion of vitamin E, its properties, occurrence, isolation and synthesis, assay, functions and uses can be found in the *Encylcopedia of Chemical Technology*, Kirk and Othmer, Volume 21, pages 574 to 585, which is incorporated herein by reference.

A serious disadvantage of all currently used methods for the separation and determination of tocopherols in food substances, in particular vegetable oils and products made therefrom, is that there occur significant losses and destruction of the isomers during the steps of the preparation and during the final quantitation. Additionally, and even more significantly, the beta-and gamma-tocopherol isomers have not satisfactorily been separated from mixtures containing these very similar dimethyl forms.

Slover et al., "Journal American Oil Chemists' Society", 44(3), 161–166, 1967, describe a gas-liquid chromatographic method for the identification and estimation of the individual tocopherols as their trimethylsilyl (TMS) ethers, after purification of the unsaponifiable matter by thin-layer chromatography (TLC). Comparison of the chromatograms of these TMS ethers for soybean oil and for wheat germ oil tocopherols indicates that this technique does not separate the gamma and beta isomers, as the gamma-tocopherol found in soybean oil has the same retention time as does the beta-tocopherol found in wheat germ oil. This procedure was investigated by the applicant and results obtained therein support the observation of lack of separation of these isomeric forms.

Lovelady, "Journal of Chromatography", 85, 81–92, 1973, as well as Lehmann, "Lipids", 6(1), 35–39, 1971, determined the individual tocopherols in plasma and red blood cells. Lovelady's method is similar to Slover's in that it involves extraction, purification of unsaponifiables by TLC, derivatization of the tocopherols, and quantitation by GLC. Lovelady reports retention times (relative to a 5,7-dimethyltocol internal standard as 1.00) for beta-tocopherol of 0.81 and for gamma-tocopherol as 0.82. Realistically, these retention times are not indicative of true separation. Moreover, for quantitation, skillful physical removal of the beta- or gamma-isomer zone, as well as the respective interface zone where the isomers intermingle from the TLC plate is required.

"Method of Analysis-AOAC", 11th Edition, Volume 54, 1971, and Nelson et al. "Journal American Oil Chemists' Society", 47(8), 259–261, 1970, discuss the analysis of tocopherols in vegetable oil, and soya sludges and residues respectively. The former is not only excessively time consuming but also results in considerable tocopherol losses. Nelson, with the advantage of dealing with the high levels of tocopherols found in sludges, was unable to separate the beta and gamma forms.

Feeter, "Journal American Oil Chemists' Society", 51(4), 184–187, 1974, determined total tocopherols in vegetable oil distillates by the Emmery-Engle reaction and the individual tocopherols as their propionate esters by GLC.

Slover, "Lipids", 6(5), 291–296, 1971, and "Journal American Oil Chemists' Society", 46(8), 417–420, 1969, reported data of tocopherol content in foods and fats, using TLC, derivatization and GLC. Christie et al., "Analyst", 98, 161–167, 1973, reported vitamin E content in food, using colorimetry for total tocopherols, and GLC for the individual isomers; again without separating the beta- and gamma-tocopherols.

Niederstebruch and Hinsch, "Fette Seifen Anstr. Mittel", 69(8), 559–563, 1967, describe determinations of tocopherols via a polarographic technique, which requires oxidation of the tocopherols to the tocopherylquinones.

Wachs and Melchert, "Deutche Lebensmittel-Rundschau", 67(7), 221–225, 1971, disclose a method wherein the unsaponifiable tocopherol is acetylated prior to quantitative analysis by GLC. Following acetylation, the esters are first refined by open-column chromatography on Sephadex LH-20 and then analyzed by GLC.

DISCUSSION OF RELATED ART

Previous art related to the separation of the tocopherols by techniques under the general genus of techniques known as liquid/solid chromatography has been limited to thin-layer chromatography (TLC). In general, this technique is limited to analytical applications, although it can be used on a preparative basis when only small amounts of compounds are required. With respect to the tocopherols, TLC has been used generally in conjunction with other techniques such as Gas-Liquid Chromatography (GLC) since the TLC alone was insufficient to effect credible separations of all tocopherol isomer forms.

Slover et al., (Infra. page 165, column 2, line 5) employs TLC as a purification technique prior to GLC, and as stated previously, was unable to achieve beta-, gamma-isomer separation. Similarly, other investigators, Lehmann J. et al., "Lipids", 6(1), 35–39, 1971; Slover, "Lipids", 6(5), 291–296, 1971; Christie, "Analyst", 98, 161–167, 1973; Aratani et al., "Journal of Chromatography", 79 179–185, 1973; Wachs et al., "Deutsche Lebensmittel-Rundschau", 67(7), 221–225, 1971; Johnson et al., "Analyst", 98, 257–267, 1973, have encountered lack of separation, detection, and identification of beta- and gamma-tocopherol mixtures on TLC since no separation could be achieved. While some have asserted beta/gamma separation, such separations were only achieved when known and equal levels of the isomers were present in standard mixtures.

Lovelady (Infra. page 89, line 2-15) used TLC for purification of fractions prior to derivatization and GLC analysis. For quantitation of either beta- or gamma-tocopherol present in mixtures of the two, Lovelady states that the desired isomer must be removed from its zone on the TLC plate. In practice, it is found that the beta- and gamma-tocopherol zones are at interface with each other, which is indicative of lack of true separation by TLC. Thus, when one of the two zones is removed, it is highly likely that it is still contaminated with remanents of the other zone.

Aratani et al., "Journal of Chromatography", 79 179–185, 1973 introduced refinements of silica gel TLC for the separation of tocopherol isomers through the use of very thin layers of absorbent, however, separation of beta-tocopherol is not mentioned in this publication.

This invention now affords a novel and rapid method for the separation of the isomers of tocopherol from mixtures thereof, including mixtures containing both beta and gamma forms. This separation now allows for quantitative determination of each of these isomers from mixtures thereof and from mixtures with food substances such as vegetable oils and products made therefrom.

SUMMARY OF THE INVENTION

Object of the Invention

An object of this invention is to provide a means for separating the alpha-, beta-, gamma- and delta-tocopherol isomers from mixtures thereof.

A further object of this invention is to provide a means for separating the aforementioned isomers from mixtures also containing beta-carotene, vitamin A, vitamin $D_2$ and mixtures thereof.

A still further object of this invention is to provide a means for separating the aforementioned mixtures from various food substances.

An additional object of this invention is to provide a means for the quantitative determination of the alpha-, beta-, gamma- and delta-tocopherol isomers in mixtures thereof.

A further object of this invention is to provide a means for the quantitative determination of aforesaid isomers and mixtures thereof, and in mixtures that also contain beta-carotene, vitamin A, vitamin $D_2$ and mixtures thereof.

A still further object of this invention is to provide a means for the quantitative determination of aforesaid isomers and mixtures in various food substances.

An even further object of this invention is to have such quantitative determination determine each isomer, including both beta and gamma forms, individually and quantitatively in a substantially short time with substantially reduced sample handling.

A still further object of the invention is to have such quantitative determination be nondestructive to the tocopherols.

Description of the Invention

The attainment of the foregoing and related objects is made possible in accordance with the present invention which in its broader aspects includes the provision of a method of separating the alpha-, beta-, gamma-, and delta-tocopherol isomers from mixtures containing these isomers comprising employing a liquid/solid phase chromatographic technique using a chloroform liquid phase, wherein said chloroform is substantially free of highly polar adjuvants or contaminants such as ethanol.

Liquid/solid phase chromatography embodies those modes of chromatography where the moving phase is a liquid and the stationary phase is a solid functioning material such as an adsorbing surface, rather than just being a support for a liquid film. Liquid/Solid Chromatography (LSC) encompasses several techniques among those including, but not limited to, Thin-Layer Chromatography (TLC), Column or "Conventional" Chromatography (CC), and relatively recently High-Performance Liquid Chromatography (HPLC) which is also known as High-Speed Liquid Chromatography (HSLC). Also encompassed within this general category are Open-column Chromatography and Gel Permeation or size exclusion Chromatography. These two latter members of the LSC family, along with column chromatography (CC), are relatively time consuming techniques, and the latter is not conducive to separation of molecules which are as close in size as those being discussed herein.

All types of chromatography are based on the phenomenon that each component in a mixture ordinarily interacts with its environment differently from all other components under the same conditions. In LSC, a dilute solution of the sample in the liquid phase is passed through a tube or column packed with a solid phase, whereupon some components in the sample will travel through the column more slowly than others resulting in the desired separation. In practice, a minimal amount of a relatively concentrated solution of the mixture to be separated is loaded into the prepared column whereupon the loading is followed by elution with additional amounts of the liquid phase. Loading, using the initial small volume is done to insure complete and efficient separation of the various components. LSC, which started out simply as column chromatography is a slow separation technique performed in vertical columns by gravity flow. Column chromatography was significantly improved by higher rates of flow brought about through increasing the pressure on the system to increase the flow rate of the liquid phase. Even greater increases in speed and versatility have been achieved by pumping the liquid phase at higher and higher column pressures up to and sometimes exceeding 1000psi. Gains in versatility have also come about through the use of smaller diameter, high surface area particles and other unique developments in packing structures and surfaces. Use of these recent innovations are the basis of HPLC.

In TLC, the solid phase, or "sorbent" or "adsorbent", as it is variously known, is deposited in a thin layer, usually 0.1–2mm thick, on a flat supporting surface. The supporting surface is normally a piece of glass and the adsorbent is generally held in place with a binding agent such as, but not limited to, starch, Plaster of Paris or other similar material. The mixture that is to be separated is dissolved in a suitable solvent, usually the liquid phase, but more likely, any fast evaporating solvent, and is applied to the solid phase as a spot a short distance from one of the ends of the plate(bands are sometimes employed in preparative modes). It is usualy desirous to have the spot be relatively small (i.e. 2–5mm in diameter) and the application can readily be achieved with a capillary tube or more preferably with a syringe. After the spotting solvent has been allowed to evaporate, the plate is then placed vertically in a developing chamber which contains the liquid phase at the bottom. Preferably, the level of the liquid phase should be about a centimeter below the point of spotting when the end of the plate is standing in the liquid phase. While this distance is not critical, the spot should, however, not be below the level of the liquid phase in the chamber. The chamber is then closed and the liquid phase is allowed to ascend the solid phase by capillary action. The development is allowed to proceed until the mixture is separated. This is usually achieved when the liquid phase front is about 10 to 15 cm above the point where the spot was originally applied, although this distance is variable within rather broad limits based upon the individual method and compounds to be separated. If selected properly, the liquid phase will resolve the original mixture into a series of spots, each optimumly corresponding to a single component of the mixture. If the materials are colored the separation will be self-visualized; however, if they are colorless, they will have to be visualized or detected by spraying them with a suitable agent to produce a color or by viewing them under special conditions, eg. ultraviolet light to cause fluorescence.

TLC is usually carried out in a chamber which has been saturated as nearly as possible with the liquid phase that will be used for the development. This is usually accomplished by having a wick, usually a piece of laboratory filter paper or the like, which partially lines the walls of the chambers.

Several terms that are frequently used in association with TLC that will facilitate understanding of this description and the examples to follow are set forth as follows. The spot containing the mixture to be analyzed is usually called the "origin", and the technique of placing it on the solid phase is known as "spotting". The "solvent front" is the top of the layer of solvent as it flows up through the chromatogram. The behavior of a specific compound in a specific chromatogram is frequently described by the "$R_f$" value. The $R_f$ value is obtained by dividing the distance moved by the solvent front into the distance moved by the compound, as measured from the center of the origin. Alternatively, "$R_s$" values are sometimes employed wherein the distance moved by some standard relative to the origin is substituted for the distance traveled by the solvent front. A more detailed treatment of this technique can be obtained by reading *Introduction of Chromatography*, Bobbett, Schwarting, and Gritter, Reinhold Boole Corporation, New York, 1968; and *Chromatography*, Heftman (Ed), Reinhold Publishing Corporation; New York, 1961 which are incorporated herein by reference. Additional background reading will also provide greater depth and understanding of this technique.

In CC, the solid or stationary phase is contained in a tube, usually cylindrical, made of glass, and closed at the bottom with a means for regulating the flow of the liquid phase from the column, such as a stopcock or valve. The solid phase may be finely divided adsorbent material or it may be an inert material supporting a liquid film. The column is usually prepared by making a slurry of the solid phase in the liquid phase and pouring the slurry into the containing column. Alternatively, the solid phase can be packed dry; however, it should usually be wetted, after packing, with the moving liquid phase so that in either case the prepared column is in contact with a liquid.

The sample mixture, dissolved in a minimum of solvent (generally the liquid phase) is placed on top of the column and is allowed to flow onto the solid phase. Generally, this loading is facilitated by reducing the level of liquid phase above the solid phase to a minimum, and then carefully pouring (to keep disruption of the solid phase to a minimum) the dissolved mixture onto the top of the solid phase. A solvent or an appropriate mixture of solvents is then allowed to flow through the column to elute the substrates. The liquid phase as it flows out of the column is known as the "effluent". In many applications of this technique, the liquid phase solvent or solvent mixture is sometimes changed during the development. Usually, solvents or mixtures thereof are sequentially added in increasing polarity. This technique is known as "gradient elution". If the correct solvents and adsorbents are chosen, hopefully, the substances to be separated will proceed down the column in concentrated bands at different rates. These bands eventually flow out with the effluent. The effluent can be continually analyzed, or fractions can be collected at known intervals corresponding to known elution times or volumes. Increased functionality can sometimes be achieved by increasing the pressure on the liquid phase to speed up elution. This is usually accomplished by having a gas line such as air or preferably an inert gas such as nitrogen attached to the column to exert pressure on the liquid phase. Various other pumping systems can be employed, however, it should be noted that the pressures involved are generally low due to the fact that the column is usually made of glass.

An alternative technique that is sometimes employed involves the stopping of the column flow prior to the emergence of any of the components of the mixture in the effluent. Usually, the solvent is allowed to run off leaving a moist adsorbent containing the separated mixture as bands on the column similar to the TLC separation. The moist adsorbent can then be extruded or pushed out of the column and the areas of the adsorbent containing the components of the mixture can then be separated physically. After the band cuts are separated, the different components can be isolated from the adsorbent with an appropriate solvent. A more detailed treatment of these techniques can be obtained by reading *Introduction to Chromatography* (infra.) and *Chromatography* (infra.) previously incorporated herein by reference.

The essential features of HPLC or modern chromatography are much the same as for CC with the exception that high pressure is employed and the column packing consists of very fine particles. These particles usually have a size range factor of two but preferably of one and one-half, and a mean diameter of between 5 and 50 microns ($\mu$m) which is about 400 mesh. The column packing may be either completely porous, such as silica gel, alumina etc., or they may be superficially porous (eg. a thin porous layer attached to a solid glass core). Additional and optional elements can include, but are not limited to, means for degassing the liquid phase, filtration systems, high pressure (3000-5000 psi) pumps, pressure gauges, dual columns, means for affecting the temperature of the columns, detectors, fraction collectors and electronic recorders. Additionally, preparative HPLC can similarly be accomplished by using higher capacity columns to accomodate the higher sample sizes usually employed. A detailed treatment of these and other related techniques is contained in *Applications of High-Speed Liquid Chromatography*, Done, Knox, and Loheac, John Wiley and Sons Inc., New York, 1974, which is incorporated herein by reference.

Application of these various techniques to the separation of the tocopherol isomers from mixtures thereof has in the past met with constant frustration, primarily due to the fact that it has been, heretofore extremely difficult if not impossible to effect a true separation of the beta and gamma isomer forms.

Applicant has now discovered that chloroform can be employed in LSC as the liquid phase to effect separations of the isomeric forms of tocopherol, including the beta and gamma forms, from mixtures containing these isomers, provided that the chloroform is substantially free of highly polar adjuvants or contaminants such as ethanol.

Although not wishing to be bound by the following statement, it is theorized that the separation achieved is dependent upon the polarity of the solvent employed as the liquid phase. It appears, however, that mere polarity alone is not the determinative factor, for not all low polar solvents will effect the separation. Again, not wishing to be bound by the following, it appears that the functionality of the solvent is dependent upon several parameters including, but not limited to hydrogen bonding, polar forces, London forces, solubility parameters and combinations thereof.

The solubility parameter contains all of the energies holding the liquid together. The major modes of interaction to be considered are dispersive (London) forces, polar forces, and hydrogen bonding. The initial approach to the division of the solubility parameter into these elements was based on a trial and error placement of the solvents as points in a three-dimensional system. This is explained in detail in "The Three Dimensional Solubility Parameter and Solvent Diffusion Coefficient", Hansen, Copenhagen, Danish Technical Press, 1967, which is incorporated herein by reference. Included under the term "highly polar adjuvants or contaminants" are any compounds or mixtures of compounds contained in the solvent either intentionally or unintentionally, which themselves have a solubility parameter sufficient, when mixed in the amount contained in said solvent, to render that solvent incapable of separating the tocopherol isomers. In general, this includes, but is not limited to, compounds with a dielectric contant ($\epsilon$) above 6. These compounds include, but are not limited to, such things as cyclohexanol, isopropanol, amyl alcohol, n-butanol, isobutanol, methylethylketone, acetone, n-propanol, ethanol, methanol, acetonitrile, glycol, furfural, glycerol, water, and mixtures thereof. By being "substantially free" of these adjuvants or contaminants is meant, that if contained at all in the liquid phase, they are present at a level of concentration low enough such that the effect of the solubility parameter of the adjuvants or contaminants will be sufficiently diminished in its effect upon the liquid phase so as not to substantially prevent separation of the various tocopherol isomers. The insidious effects associated with the use of solvents is a recognized problem in the art, especially with batch to batch variation associated with commercial solvents which may affect absolute retention times and thus cause confusion if daily reference standards are not run. The problem is set forth in a Waters Associates manual "Liquid Chromatography - A practical Approach" on page 24 of that manual as follows:

"A more insidious problem may arise in the use of solvents. That is the bottle-to-bottle, batch-to-batch variation of impurities that are always present in commercially purchased solvents. An example of this is that analytical reagent-grade chloroform contains from 0.7 to 1% by weight of ethanol. This is put in as a stabilizer so that if chloroform is reduced in volume on a hot plate, phosgene will not be produced. Variations in the level of alcohol and the kind of denaturants used in the alcohol added to the chloroform may make varying alterations in the retention volumes of the separations. The alcohol will partially deactivates a siliceous support and, if the level of alcohol varies, varying degrees of deactivation will occur. Because there may be interaction of solvent with the separation mechanism, careful choice of purity is necessary."

The most efficient method of separating the isomers of tocopherol is by HPLC. Included in this technique are preparative modes wherein the size of the column may be increased to allow for increased amounts of mixtures to be separated. While individual HPLC systems can be constructed to suit the particular application it is preferable to employ one of the commercially available HPLC units. These units include, but are not limited to, Waters ALC 202, Perkin-Elmer's Models 601 and 604, Du Pont's Models 848 and 830 and Waters Associates Prep LC/System 500.

With respect to HPLC, several functioning solid phases may be employed. Generally, any siliceous packing suitable for HPCL will work. Usually these packings consist of very fine particles having a mean diameter of between 5 and 50 $\mu$m. A more preferable range, and one that is more commonly used is from 5 to 30 $\mu$m. The most preferable solid phase is a porous silica with an average particle size of about 10 $\mu$m. Generally, these particles have a rather large surface area. Usually the surface area is above about 150 square meters per gram of packing. Preferably, the surface area is about 250 to about 500 square meters per gram and most preferably the packing should have a surface area of about 300 to 400 square meters per gram. These high surface areas are required to effect separations and increase efficiency. Many packings are functional and they include, but are not limited to, the following commercially available packings sold under the trade names of Porasil, μ Porasil, Corasil, and Alumina as supplied by Waters Associates, and Partisil 10 as supplied by Whatman Inc. Partisil is a silica gel of 10 μm particle size and is supplied by Whatman in columns for HPLC. Porasil is a fully porous particle while Corasil is pellicular. Both are fairly close in size with Porasil having particles ranging from 37–75 μm in size and Corasil having particles ranging 37–50 μm is size. μ Porasil has a particle size of about 10 μm. Columns can be prepared by the individual worker, however, since they are difficult to pack, it is usually convenient to purchase a commercially prepared column. These columns vary in dimension. For example, Waters commercially produces a μ Porasil column with dimensions of 4 mm ID × 30 cm. A Corasil column is available with dimensions of 2mm ID × 61 cm. A great degree of variability in column dimension is allowable and the dimensions are not critical. However, while not critical, certain column parameters produce more advantageous results than others and one skilled in the art can readily determine these parameters with simple experimentation. Generally, special preparative chromatographic columns for Preparative HPLC (PHPLC) are quite similar to those described above and differ simply in that they usually are of greater size thereby allowing larger sample mixtures to be separated. Again, it is preferable to employ commercial columns as they generally perform more consistently than those made at the bench. Recently, a new method of fabricating PHPLC columns has been developed using Radial Compression Technology. This technique, which is the subject of a pending patent application to Waters Associates involves transforming a flexible walled cylinder or cartridge, filled with chromatographic medium, into a high efficiency column by radial compression. Columns manufactured by this technique are currently being marketed by Waters Associates Inc. under the trademark designation Prep PACK 500. These columns are 5.7 cm × 30 cm in size and contain clean dry silica as the solid phase.

Initial work with HPLC was performed using commercially available laboratory reagent grade chloroform as the liquid phase. It was found by using this material that separation could be achieved between the trimethyl, dimethyl and methyl forms of tocopherol. Unfortunately, separation between the beta and gamma forms (the dimethyl isomers) was not achieved and these two isomeric forms were eluted with exactly the same retention time or at least with retention times so close that the peaks appeared to be one in the same on the recording equipment attached to the HPLC system. Through experimentation, it was found that if the commercial reagent grade chloroform was extracted several times with water and was thereupon dried with a commercially available drying agent, the resulting chloroform could be employed to substantially separate the beta and gamma forms as well as the alpha and delta forms of tocopherol. While the separation of these forms was substantially complete some interfacing was noticed between the beta and gamma isomers. Analysis of the water-extracted chloroform disclosed that the ethanol content of this reagent grade chloroform was not at trace levels (i.e. <0.01% ethanol). Based upon this discovery it was decided to further experiment using "ethanol-free" chloroform. Ethanol-free chloroform was obtained from Burdick and Jackson Laboratories Inc. This solvent is distilled in glass and is packed under nitrogen. Similar grades can be obtained through various suppliers or can be made in the laboratory. When the ethanol-free chloroform was used as the liquid phase in HPLC, complete separation was evidenced between all isomeric forms of tocopherol including the beta and gamma isomers. The various methods that can be employed in achieving these separations by HPLC will become more readily understandable in the example section to follow shortly.

Further experimentation showed the mixtures of tocopherols could also be separated from mixtures containing beta-carotene, vitamin A and vitamin $D_2$ as well as mixtures thereof. It was also discovered, that these other components of the mixture would separate individually and completely by HPLC.

In practice, the mixture to be separated is solubilized in a small amount of the liquid phase. Optimumly, this solution can be a known volume to facilitate calculations when the method is to be employed for quantitative analysis. An aliquot of this solution, usually taken with a microliter syringe, is then injected onto the column of the HPLC system, and is then eluted with additional amounts, sufficient to separate the isomers, of the ethanol-free chloroform. The elution is continued until all desired isomeric forms are sequentially eluted from the column. The separate forms can then either be collected or analyzed in line by use of any one or a combination of known analytical techniques. These techniques have been outlined previously. In the preferred mode quantitative ultra-violet (UV) spectroscopy is usually employed.

In the instances where the mixture is present in a food substance such as vegetable oil or for example a margarine, it is usually desirable to effect a separation of the mixture of tocopherols from the other major components of the food substance. This separation is performed preliminarily to the chromatographic separation and comprises the elements of saponifying the food substance and subsequently extracting the unsaponifiable tocopherols from the resulting saponified matter. It should be noted, that while the saponification and extraction could be carried out under normal laboratory conditions, the tocopherols are extremely liable to photo-induced oxidation. For this reason, it is preferable to undertake this preliminary procedure in a manner to substantially reduce the chance of this oxidation. This can be achieved by the use of Amberglass-Quality glassware and/or lighting that substantially excludes ultra-violet radiation. It is also preferable to employ the use of an inert atmosphere such as, but not limited to nitrogen or helium during this technique. A greater understanding of this preliminary technique will become more readily understandable in the example section to follow.

In case of preparative HPLC, a column of larger size allowing substantially larger amounts of material to be separated can be employed should separation of large quantities be desired. However, standard equipment as described herein can be employed for preparation work using smaller amounts of the mixtures. As in analytical HPLC, in preparative HPLC, (PHPLC) ultraviolet detection or other similar analytical tools can be employed to indicate the moment when elution of a particularly desired isomeric form has taken place ensuring the collection of that specific form.

Another LSC method for the separation of the tocopherol isomers is TLC. Included in this technique are preparative and analytical modes. In preparative TLC, individual fractions can be mechanically lifted from the developed plate. However, due to the relative ease of PHPLC, this technique is preferred over the preparation TLC technique.

Several solid phases can be employed in TLC as sorbents, however, those usually preferred as silica gels. In the preferred mode a silica gel with a particle size of 250 μ is usually employed. This material is preferably coated on a glass plate. Again, in the preferred mode, ethanol-free chloroform is found to effect the optimum separation. As with the experience gained in HPLC, extraction with water of the reagent grade chloroform and subsequent drying was found to produce substantially satisfactory separations of the alpha-, beta-, gamma- and delta-forms with only slight interfacing between the beta and gamma isomers. Use of ethanol-free chloroform resulted in complete separation. TLC techniques are well known in the art and parameters can be established easily by one skilled in the art for his particular application. In general, the mixture to be separated is spotted on the TLC plate and is then developed with the appropriate solvent. In the preferred mode this solvent is ethanol-free chloroform. The development is usually, as indicated previously, carried out in a tank that has been equilibrated with the liquid phase. In the preferred mode, development should be carried out until the solvent front moves about 15 cm from the orgin which itself is about 2 cm from the end of the plate. Time of development is found to be about 30 to 45 minutes, however, the time is not critical. Detection in TLC can be accomplished by various techniques known in the art. These include, but are not limited to, viewing under a UV light source, iodine vapor color development, phosphomolybdic acid color development and other known techniques. When phosphomolybdic acid is employed, a 3.5% solution in isopropyl alcohol applied as an atomized spray, or the use of various commercial forms in an aerosol-propelled medium, it produces excellent results for visualization of the tocopherols.

All parts and proportions herein and in the appended claims are by weight unless specified otherwise.

The instant invention will be more fully understood by reference to the following examples considered in the light of the drawings all of which are presented for illustrative purposes, and are not to be interpreted as limiting the scope of the invention.

BRIEF DESCRIPTION OF DRAWINGS

In the FIGS. 1 through 3 are shown three comparative High Performance Liquid Chromatography Chromatograms.

FIG. 1 is a representation of a HPLC chromatogram of tocopherol isomers using reagent grade chloroform.

FIG. 2 is a representation of a HPLC chromatogram of tocopherol isomers using reagent grade chloroform from which the ethanol preservative has been extracted.

FIG. 3 is a representation of a HPLC chromatogram of tocopherol isomers using ethanol-free chloroform. These Figures and Drawings are discussed in detail in Example 3.

FIG. 4 shows a Thin-layer Chromatography chromatogram of tocopherol isomers and of a margarine sample containing various tocopherols. This Figure is discussed in detail in Example 9.

EXAMPLE 1

A. Reagent Preparation

Reagent grade chloroform proported by its labeling to contain 0.7-1.0% ethanol (v/v) as a preservative was extracted with an equal volume of water. After the two liquids were shaken in a separatory funnel, the layers were allowed to separate, and the chloroform fraction was withdrawn to a second separatory funnel wherein the extraction was repeated. After the second extraction, the chloroform phase was again removed to a third separatory funnel whereupon the extraction was repeated for a third time with another equal volume of water. After the third extraction, the chloroform phase was passed through anhydrous sodium sulfate to dry the solvent.

B. Comparison of Ethanol Concentrations in Various Sources of Chloroform

Reagent grade chloroform, chloroform as prepared in Example 1(A), as well as "Ethanol-free" chloroform were analyzed by Gas liquid Chromatography to determine the amounts of ethanol contained therein. Samples were analyzed using isopropyl alcohol as an internal standard. A sample of known weight of each of the chloroforms were spiked with a known weight of isopropyl alcohol. An aliquot of each mixture was shot onto a GLC column specific for separating various alcohols. Calculation of the resulting peaks indicated the following levels of ethanol:

| Description of Chloroform | % Ethanol (w/w) |
| --- | --- |
| Reagent Grade $CHCL_3$ | 0.33% |
| $CHCL_3$ treated as per Example 1(A) | Nil (no peak) |
| Burdick & Jacksons Ethanol-free $CHCL_3$ | Nil (no peak) |

As is evident from the data, chloroform extracted as described in Example 1(A) can be rendered substantially free of ethanol. The discrepancy between the label value of 0.7-1% and the determined value of 0.33% can be explained by the fact that the label percent is given on a volume/volume (v/v) basis wherein the experimentally determined value is on a weight/weight (w/w) basis. Taking into account the differences in density between chloroform and ethanol account for the observed variation.

C. Comparison of HPLC Chromatograms of α-, β-, γ- and δ-Tocopherol Obtained by Using the Chloroforms of Example 1(B)

HPLC Chromatograms for a known mixture of α-, β-, γ- and δ-tocopherol were run using the various chloroforms described in Example 1(B) (including that prepared by Example 1(A).

A standard mixture of the four isomeric forms of tocopherol was prepared containing approximately equal parts of α-, β-, γ- and δ-tocopherol. Approximately 25 mg of the mixture was made up in petroleum ether to a volume of about 10 mls. From this standard solution, three individual alequots of about 0.5 mls each were transferred to each of three test tubes whereupon the petroleum ether was gently evaporated using a stream of nitrogen gas. Each of the three samples was then dissolved in about 0.5 ml of one of the chloroforms; i.e. one was dissolved in the treated chloroform (Example 1(A) one was dissolved in the reagent grade chloroform, and the third was dissolved in the ethanol-free chloroform. Successively, about 25 μl of each of the above solutions were then injected onto a High Performance Liquid Chromatographic column which is described along with its operating conditions as follows:

| | |
|---|---|
| Instrument | Waters Associates' Model ALC 202 |
| Column | μ Porasil, 4 mm DD × 30 cm |
| Liquid Phase | As described above (Liquid phase corresponds to the solvent used to dissolve the tocopherol mixture prior to injection.) |
| Mode of Operation | Isocratic |
| Flow Rate of Liquid Phase | 1 ml/min. |
| Detector | UV set at 254 nm 0.16 AUFS (Absorvance Units Full Scale) |
| Recorder | Dual-pen, Serve-Rite II, by Texas Instruments Inc. |
| Chart Speed | 12 in/hr. |

Representations of the resulting chromatograms are shown comparatively in FIGS. 1, 2, and 3.

FIG. 1 represents the chromatogram obtained by employing, as the liquid phase, reagent grade chloroform, containing approximately 0.7% (v/v) ethanol as a perservative. The horizontal axis represents elution time while the vertical axis represents absorbance at 254 μm at about 0.16 absorbance units full scale deflection. An inverse inflection of the base line is noted at the time of injection, with three major peaks following in succession. The first is believed to be that of alpha-tocopherol. The second due to its size is believed to contain two isomers, most likely the beta- and gamma-tocopherol. The third peak is believed to be for delta-tocopherol. No attempt was made to determine the chemical identity of each peak and the assumptions made above are based on the data associated with the separation achieved using HPLC with ethanol-free chloroform. The reasons for these assumptions will become more clear later in this example. The important observation is, that reagent grade chloroform could not resolve the four tocopherol isomers into four distinct peaks.

FIG. 2 represents the chromatogram obtained employing treated reagent grade chloroform (see Example 1(A) as the liquid phase. Again, the horizontal axis represents elution time while the vertical axis represents absorbance at 254 ηm at about 0.16 absorbance units full scale deflection. As in the previous Figure an inflection is noted at the time of injection. Four major peaks follow in succession. The first major peak is believed to correspond to the alpha-tocopherol isomer. This peak is then followed by two other major peaks, which although substantially separated, do not separate to baseline. The paired peaks are believed to be gamma- and beta-tocopherol. The last peak is believed to be due to delta-tocopherol. Again, no attempt was made to determine the chemical identity of each peak and the assumption as to identify are made on the experience obtained from the data associated with the HPLC using ethanol-free chloroform. The reasons for these assumptions will become more evident later in the example. The important observation is, that treated chloroform (as obtained from example 1(A) can effectively resolve the four tocopherol isomers into four distinct peaks.

FIG. 3 represents the chromatogram obtained employing ethanol-free chloroform as the liquid phase. Again, the horizontal axis represents elution time while the vertical axis represents absorbance at 254 νm at about 0.16 absorbance units full scale deflection. As in the previous Figures, an inflection is noted at the time of injection. Again, as previously observed, this inflection is closly followed by four distinct major peaks. Each of these peaks is resolved to baseline unlike the case as shown in FIG. 2 wherein two peaks were seen to interface. The four major peaks in order of elution are alpha-tocopherol, gamma-tocopherol, beta-tocopherol, and delta-tocopheral. Total elution time represented by the chromatogram, as with the two previous examples, was less than about forty-five minutes. The manner whereby the individual peaks were identified will be discussed in following Section D. Under the conditions as stated above the elution times for the various isomers are as follows:

| | Elution Time |
|---|---|
| alpa-tocopherol | ~10.1 minutes |
| gamma-tocopherol | ~17.0 minutes |
| beta-tocopherol | ~19.7 minutes |
| delta-tocopherol | ~32.3 minutes |

These elution or retention times are measured from the point of injection.

D. Identification of Chromatogram Peaks

The identification of the various peaks in the chromatograms of Section C of this Example was carried out by various analytical techniques. Since the separation accomplished by the ethanol-free chloroform liquid phase proved to be the most definitive mode, fractions isolated by this technique were subjected to further analysis for identity. Since it is extremely unlikely that the order of elution would be different for the treated chloroform (Section C, FIG. 2) and for the ethanol-free chloroform, identification of peaks from the latter are considered predictive for the former.

1.1. Comparison of Elution Times

As stated in Section C, the elution times of the major peaks using ethanol-free chloroform under the conditions stated were about: 10.1, 17.0, 19.7, and 32.3 minutes respectively for alpha-, gamma-, beta-, and delta-tocopherol. Individual solutions of each of alpha-, beta-, gamma-, and delta-tocopherol standards were prepared as was the mixture of Section C. These individual standards were then run on the HPLC unit to determine the elution time of each individual isomer under the conditions of Section C using ethanol-free chloroform as the liquid phase.

Alpha-tocopherol demonstrated an elution time of about 10.1 minutes. Thus it is concluded that the first major peak of the chromatogram shown in FIGS. 2 and 3 is due to alpha-tocopherol.

Beta-tocopherol demonstrated an elution time of about 19.7 minutes. Thus it is concluded that the third major peak of the chromatogram shown in FIGS. 2 and 3 is that corresponding to beta-tocopherol.

Gamma-tocopherol demonstrated an elution time of about 17.0 minutes. Thus it is concluded that the second major peak of the chromatogram shown in FIGS. 2 and 3 is that corresponding to gamma-tocopherol.

Delta-tocopherol demonstrated an elution time of about 32.3 minutes. Thus it is concluded that the fourth major peak of the chromatogram shown in FIGS. 2 and 3 is that corresponding to delta-tocopherol.

2.1. Fraction Identification by Spectroscopy

An HPLC run was made on a known mixture of tocopherol isomers using ethanol-free chloroform as the liquid phase and the instrument conditions as set forth in Section C. As the individual isomers were eluted, fractions of the eluent were collected corresponding to the observed peaks for alpha-, beta-, gamma-, and delta-tocopherol. These fractions were collected by using the signal generated by the UV detector in the HPLC to let the operator know the exact moment of isomer elution. Fractions of the eluent were collected to test tubes, and the liquid phase was evaporated off under nitrogen to yield dry samples of tocopherol isomers. These fractions were labeled A, G, B, and D corresponding to the elution times for alpha-, gamma-, beta-, and delta-tocopherol as determined above.

Mass spectra on these fractions indicated the following information:

1. Mass spectra for fractions A, B, G, and D correspond exactly to those run on standards of alpha-, beta-, gamma-, and delta-tocopherol respectively.

2. Mole weight determinations by mass spectroscopy for fractions B and G as well as for beta- and gamma-tocopherol standards showed measured mole weights of 416 grams/mole.

3. Mole weight determinations by mass spectroscopy for fraction A and alpha-tocopherol standard was found to be 430 grams/mole. Similarly, mole weights for fractions D and delta-tocopherol standard were measured as being 402 grams/mole.

NMR spectra were run on fractions A, B, and G as well as on standards of alpha-, beta-, and gamma-tocopherol. The alpha-tocopherol standard showed no NMR proton activity around 5.0 to 7.0δ. The gamma-tocopherol standard showed a peak of about 6.18δ. The beta-tocopherol standard showed a peak of about 6.31δ. These peaks are believed to correspond to the aromatic proton in these two isomers. NMR spectra of the fractions separated as per Section C showed an NMR peak at about 6.18δ for the G fraction, and a peak at about 6.31δ for the B fraction. No peak was evidenced for the A fraction between 5.0 and 7.0δ.

From the above, it was concluded that the isomers of tocopherol had been successfully separated and identified.

EXAMPLE 2

A. Separation of Tocopherol Isomers From Food Substances

The following gives a detailed example for the preparation of a vegetable oil type products, for subsequent separation of the tocopherols contained therein by chromatography.

Approximately about 0.2 to about 0.8 grams of sample is accurately weighed into a 500 ml Amberglass Erlenmeyer flask with 24/40 joint. To this are added 200 mg of pyrogallol (to act as an anti-oxidant), 100 ml of 200-proof ethanol and Teflon boiling chips. The flask is then connected to an additive adaptor, having a reservoir of about 100 ml, and to a water condenser. The apparatus is then flushed with nitrogen for about five minutes. Through the reservoir are then added about 5 ml of saturated aqueous potassium hydroxide solution. The apparatus is then heated using a hot plate to bring the mixture to reflux under a nitrogen atmosphere. After refluxing for about five minutes, the still assembled apparatus is transferred, still under nitrogen, such that the flask is cooled in an ice bath. After the mixture has cooled, 100 ml of petroleum ether and 100 ml of ice cold distilled water are added through the reservoir. The Erlenmeyer flask is then disconnected from the adapter-condenser system whereupon the flask is closed using a stopper. Once closed, the flask is shaken for about 2 minutes with cautious venting of any pressure.

After shaking, the contents of the Erlenmeyer flask are transferred to a 500 ml separatory funnel and the two phases are allowed to separate. The lower, aqueous phase is removed to a second 500 ml separatory funnel containing a second 100 ml portion of petroleum ether. This admixture is then shaken for about one minute. The aqueous phase of this extraction is then discarded and the two petroleum fractions are combined in one of the separatory funnels. The empty funnel is then washed twice with small amounts of petroleum ether and the washings are added to the combined petroleum ether extracts.

About 2 ml of a 10% ethanolic pyrogallol solution are added to about 100 ml of ice cooled water and this in turn is added to the combined ether extracts. The phases are shaken thoroughly for about 1 minute and, allowed to separate, whereupon the aqueous phase is discarded. These water washings are repeated three more times. The washed petroleum ether phase is then transferred, stepwise and quantitatively, into a centrifuge tube (capacity 40–50 ml) and the petroleum ether is evaporated to dryness under nitrogen in a water bath at about 35° C.

The dry residue in the test tube is the unsaponifiable matter containing the tocopherols. This fraction is now ready for chromatographic separation. If the separation is not going to be carried out on the day of extraction the residue should be left in a small amount of petroleum ether and be stored under refrigeration and an inert atmosphere.

B. Determination of Tocopherol Content in Vegetable Oils

Various refined and bleached vegetable oils were analyzed using the sample preparation technique of Example 2 A and the HPLC technique of Example 1 C with ethanol-free chloroform as the liquid phase. The results of these analyses are shown in Table 1. Concentrations were determined quantitatively by comparison of responses of sample peaks to responses for peaks of known weights of standards (external standard calibration method).

Various previously reported values for the tocopherol content of specific oils, are given for Corn Oil, Soybean Oil, Safflower Oil, Sunflower Oil and Cottonseed Oil in Tables 2, 3, 4, 5, and 6 respectively. These values are included for a comparison with the analysis contained herein. Differences with respect to some historically reported values are attributed to the increased functionality of the instant method.

Table 1

| Tocopherol Content of Vegetable Oils (mg/100g) AS DETERMINED IN 2 B | | | | |
|---|---|---|---|---|
| Oil Sample | α-Tocopherol | β-Tocopherol | γ-Tocopherol | δ-Tocopherol |
| Corn Oil | 8.2 | 9.6 | 39.6 | 33.7 |
| Cottonseed Oil | 28.0 | 4.1 | 41.1 | 8.0 |
| Palm Oil | 26.0 | 25.0 | Trace | 3.0 |
| Safflower Oil | 36.1 | 7.3 | 7.3 | 4.2 |
| Soybean Oil | 9.1 | Trace | 59.7 | 32.4 |
| Sunflower Oil | 68.0 | 8.0 | 5.8 | Trace |

Table 2
Comparative Data of Tocopherol Content for Corn Oil (mg/100g)

| Sample Treatment | α | β | β+γ | γ | δ | Source |
|---|---|---|---|---|---|---|
| purified and deodorized | 7.9 | — | — | 44.7 | — | Slover et. al.; JAOCS; 46(8). p417–420 |
| health-food grade | 16.2 | — | — | 60.3 | — | Slover et. al.; JAOCS; 46(8), p417–420 |
| no description | 11.2 | 5.0 | — | 60.2 | 1.8 | Slover; "Lipids"; 6(5); p 291–296 |
| no description | 11.9 | — | 39.5 | — | 0 | Christie et. al.; "Analyst"; 98; p 161–167 |
| no description | 12–22 | — | — | 46–75 | 4–5 | Carpenter et. al.; AOCS Meeting Mexico City 1974 |
| refined and bleached | 8.2 | 9.6 | — | 39.6 | 33.7 | Applicant (Example 2  B) |

Table 3
Comparative Data of Tocopherol Content for Soybean Oil (mg/100g)

| Sample Description | α | β | β+γ | γ | δ | Source |
|---|---|---|---|---|---|---|
| purified and deodorized | 4.2 | — | — | 25.2 | 5.3 | Slover et. al.; JAOCS; 46(8); p 417–420 |
| health-food grade | 9.4 | — | — | 63.0 | 23.2 | Slover et. al.; JAOCS; 46(8); p 417–420 |
| no description | 10.1 | — | — | 59.3 | 26.4 | Slover; "Lipids"; 6(5); p 291–296 |
| specially processed | 5–14 | — | — | 68–103 | 11–37 | Carpenter et. al.; "Analyst"; 98 p 161–167 |
| cold processed | 9 | — | — | 68 | 23 | Carpenter et. al.; "Analyst"; 98 p 161–167 |
| refined | 3.5 | — | 21.0 | — | 11.5 | Wachs et. al.; "Deutsche Lebensmittel-Rundschau"; 67(7) p 221–225 |
| refined and bleached | 9.1 | Trace | — | 59.7 | 32.4 | Applicant (Example 2  B) |

Table 4
Comparative Data of Tocopherol Content for Safflower Oil (mg/100g)

| Sample Description | α | β | β/γ | γ | δ | Source |
|---|---|---|---|---|---|---|
| No description | 34.2 | — | — | 7.1 | — | Slover et. al.; JAOCS; 46(8); p 417–420 |
| No description | 38.7 | — | — | 17.4 | 24.0 | Slover; "Lipids"; 6(5); p 291–296 |
| No description | 48–60 | — | — | — | — | Carpenter et. al.; "Analyst"; 98; p 161–167 |
| Refined and bleached | 36.1 | 7.3 | — | 7.3 | 4.2 | Applicant (Example 2  B) |

Table 5
Comparative Data of Tocopherol Content for Sunflower Oil (mg/100g)

| Sample Description | α | β | β/γ | γ | δ | Source |
|---|---|---|---|---|---|---|
| No description | 48.7 | — | — | 5.1 | 0.8 | Slover; "Lipids"; 6(5); p 291–296 |
| Refined | 53.0 | — | 4.5 | — | 0.5 | Wachs et. al.; "Deutche lebensmittel-Rundshau" p 221–225 |
| Refined and bleached | 68.0 | 8.0 | — | 5.8 | Trace | Applicant (Example 2  B) |

Table 6
Comparative Data of Tocopherol Content for Cottonseed Oil (mg/100g)

| Sample Description | α | β | β/γ | γ | δ | Source |
|---|---|---|---|---|---|---|
| Purified and deodorized | 32.0 | — | — | 31.3 | — | Slover et. al.; "JAOCS"; 46(8) p 416–420 |
| No description | 38.9 | — | — | 38.7 | — | Slover; "Lipids"; 6(5); p 291–296 |
| Refined and bleached | 28.0 | 4.1 | — | 41.1 | 8.0 | Applicant (Example 2 B) |

EXAMPLE 3

Reproducibility of Analysis For Tocopherol Content in Margarine Samples

Margarine samples were analyzed using the sample preparation of Example 2  A, and the HPLC technique of Example 1  C with ethanol-free chloroform as the liquid phase. The results of these analyses are given in Tables 7 and 8. Table 7 shows six repetitions for margarine "P" having a safflower oil base. Mean values and standard deviations, given by X̄ and S.D. respectively, are also shown. It was shown that margarine "P" contained about 14.8 mg/100g of alpha-tocopherol, and 4.5 mg/100g of gammatocopherol. Values for beta-tocopherol and delta-tocopherol were not calculated. Margarine "I" was shown to contain about 7.2 mg/100g of alphatocopherol and about 28.9 mg/100g of gamma-tocopherol. Again, values for beta-tocopherol and delta-tocopherol were not calculated.

As can be seen, reproducibility of analysis is excellent for the various repetitions.

Table 7
Margarine Sample "P" Tocopherol Content in mg/100g (Reproducibility of Analysis)

| Repetition | α-Tocopherol mg/100g | γ-Tocopherol mg/100g |
|---|---|---|
| 1 | 14.4 | 4.4 |
| 2 | 16.7 | 5.1 |
| 3 | 13.7 | 4.1 |
| 4 | 14.4 | 4.5 |
| 5 | 14.2 | N.R. |
| 6 | 15.1 | N.R. |
| X̄ | 14.8 | 4.5 |
| S.D. | 1.06 | 0.42 |

N.R. = Not Run

Table 8
Margarine Sample "T" Tocopherol Conetent in mg/100g (Reproducibility of Analysis)

| Repetition | α-Tocopherol mg/100g | γ-Tocopherol mg/100g |
|---|---|---|
| 1 | 7.3 | 28.7 |
| 2 | 7.0 | 30.0 |
| 3 | 7.4 | 28.0 |
| 4 | 7.0 | N.R. |
| X̄ | 7.2 | 28.9 |

Table 8-continued

| Margarine Sample "T" Tocopherol Conetent in mg/100g (Reproducibility of Analysis) | | |
|---|---|---|
| Repetition | α-Tocopherol mg/100g | γ-Tocopherol mg/100g |
| S.D. | 0.21 | 1.02 |

N.R. = Not Run

EXAMPLE 4

Analysis of Margarine Samples For α-, β-, γ-, δ-Tocopherol Content

Margarine samples were analyzed using the sample preparation technique of Example 2 A, and the HPLC technique of Example 1 C with ethanol-free chloroform as the liquid phase. Results are shown in Table 9. These data shown the varying content of tocopherol isomers and hence vitamin E activity available from various commercial products.

Table 9

| | Tocopherol Content in Margarines (mg/100g) | | | | |
|---|---|---|---|---|---|
| Sample | Main Oil Base | α | β | γ | δ |
| "F" | Corn Oil | 7.0 | 4.5 | 34.5 | 7.3 |
| "I-T" | Soybean Oil | 5.9 | 19.0 | 31.3 | 9.5 |
| "P-T" | Safflower Oil | 22.0 | 17.8 | 5.6 | 16.3 |
| "P-T" | Sunflower Oil | 36.0 | 16.1 | 10.1 | 8.3 |

EXAMPLE 5

TLC Chromatogram of α-, β-, γ-, and δ-Tocopherol

TLC was used to separate the various isomers of tocopherol. A representation of the TLC plate is shown in FIG. 4. A 20 cm × 20 cm silica gel (250 μ particle size) plate 1 was spotted along an imaginary reference line 2 with alpha-tocopherol 3, beta-tocopherol 5, gammatocopherol 4, and delta-tocopherol 6. In addition, a known mixture of alpha-, beta-, gamma-, and delta-tocopherol was spotted 7 as well as a sample of the unsaponifiable matter from margarine (P-T$_2$) from Example 4 as prepared by the procedure of Example 2 A, 8. Once the spots 3, 4, 5, 6, 7 and 8 had dried, the plate was allowed to be developed in a TLC chamber saturated with and using ethanol-free chloroform as the liquid phase. The plate was allowed to develop until the solvent front 9 had traveled a total distance of 15 cm from the point of spotting. Once the plate had been removed from the chamber and dried, it was visualized with 3.5% phosphomolybdic acid in isopropyl alcohol. A spot 10 showed that alpha-tocopherol had an $R_f$ value of 0.47. A spot 11 showed an $R_f$ value of 0.30 for gamma-tocopherol. A spot 12 yielded an $R_f$ value of 0.23 for beta-tocopherol. A spot 13 yielded an $R_f$ value of 0.14 for delta-tocopherol. The separation of the spot for the known mixture of tocopherols 7 yielded four distinct spots 17, 16, 15, and 14 corresponding to separation of delta-, beta-, gamma-, and alpha-tocopherol respectively. The $R_f$ values for the known mixture are identical to those measured for the individual standards. The spot 8 corresponding to the P-T$_2$ margarine of Example 4 separated into four distinct spots 18, 19, 20, and 21 whose $R_f$ values corresponded exactly to delta-, beta-, gamma-, and alpha-tocopherol. A fifth spot 22, with a higher $R_f$ value than alpha-tocopherol is believed to be due to hydrocarbons present in the unsaponifable fraction (eg. beta carotene).

What is significant to note is that a total separation has been achieved by TLC for beta- and gamma-tocopherol.

It is to be further understood that in light of the instant specification that this invention is capable of variation and modification without departing from the scope thereof.

What is claimed is:

1. In a method for separating the alpha-, beta-, gamma- and delta-tocopherol isomers from mixtures thereof employing High-Performance Liquid Chromatography,
the improvement comprises using chloroform as the chromatographic liquid phase, wherein said chloroform is substantially free of highly polar adjuvants or contaminants.

2. A method according to claim 1 wherein said mixture also contains at least one compound selected from the group consisting of betacarotene, vitamin A, vitamin D$_2$.

3. A method according to claim 1 wherein the steps of said method comprise:
   a. dissolving said mixture in said chloroform;
   b. loading said dissolved mixture on a solid phase, wherein said solid phase comprises a siliceous chromatographic medium wherein said medium has an effective surface area of at least 150 square meters per gram, and further wherein the particles of said medium have a mean diameter between about 5 and 50 microns; and
   c. eluting said solid phase with additional quantities, sufficient to elute said isomers, of said liquid phase.

4. A method according to claim 3 further comprising: determining the concentrations of said eluted isomers in said liquid phase, by conventional analytical techniques.

5. A method according to claim 4 wherein said conventional analytical technique is quantitative ultra-violet spectroscopy.

6. A method according to claim 4 wherein said solid phase is a porous silica packing material with an average particle size of about 10 microns and a surface area of about 350 square meters per gram.

7. A method according to claim 6 wherein said mixture also contains at least one compound selected from the group consisting of beta-carotene, vitamin A, vitamin D$_2$.

8. A method according to claim 6 where said mixture is first separated from a food substance by preliminary procedure comprising:
   a. saponifying said food substance to produce a reaction mixture; and
   b. extracting the unsaponified tocopherols from the reaction mixture.

9. A method according to claim 8 wherein said preliminary procedure is carried out in an inert atmosphere, and is substantially protected from sources of ultra-violet light radiation.

10. In a method of separating the alpha-, beta-, gamma- and delta-tocopherol isomers from mixtures thereof employing Thin-Layer Chromatography, the improvement comprises
using chloroform as the chromatographic liquid phase, wherein said chloroform is substantially free of highly polar adjuvants or contaminants.

11. A method according to claim 10 wherein said mixture also contains at least one compound selected from the group consisting of beta-carotene, vitamin A, vitamin D$_2$.

12. A method according to claim 10 wherein the steps of said method comprise:
   a. applying said mixture to a chromatographic plate, said plate comprising a sorbent coated on a hard surface; and
   b. developing said plate with said liquid phase.

13. A method according to claim 12 wherein said sorbent comprises a silica gel of a particle size of about 250 microns.

14. A method according to claim 13 wherein said mixture also contains beta-carotene, vitamin A, vitamin $D_2$, and mixtures thereof.

15. A method according to claim 13 wherein said mixture is present in a food substance where said mixture is first separated from said food substance by a preliminary procedure comprising:
   a. saponifying said food substance to produce a reaction mixture; and
   b. extracting the unsaponified tocopherols from the reaction mixture.

16. A method according to claim 15 wherein said saponification is carried out in an inert atmosphere, and is substantially protected from sources of ultra-violet light radiation.

17. A method according to claim 1 wherein said High-Performance Liquid Chromatography is preparative chromatography.

18. A method according to claim 17 wherein said mixture is contained in a sludge by-product derived from the deodorization of finished edible oils.

* * * * *